(12) United States Patent
Tuan Ismail et al.

(10) Patent No.: US 9,303,276 B2
(45) Date of Patent: Apr. 5, 2016

(54) METHOD TO PRODUCE HYDRAZIDE

(71) Applicants: Malaysian Palm Oil Board, Selangor Darul Ehsan (MY); Universiti Putra Malaysia, Serdang (MY)

(72) Inventors: Noor Maznee Tuan Ismail, Selangor Darul Ehsan (MY); Hazimah Abu Hassan, Selangor Darul Ehsan (MY); Wan Md Zin Wan Yunus, Serdang (MY)

(73) Assignees: Malaysian Palm Oil Board, Selangor Darul Ehsan (MY); Universiti Putra Malaysia, Serdang (MY)

( * ) Notice: Subject to any disclaimer, the term of this patent is extended or adjusted under 35 U.S.C. 154(b) by 0 days.

(21) Appl. No.: 14/357,531

(22) PCT Filed: Nov. 7, 2012

(86) PCT No.: PCT/MY2012/000270
§ 371 (c)(1),
(2) Date: May 9, 2014

(87) PCT Pub. No.: WO2013/070059
PCT Pub. Date: May 16, 2013

(65) Prior Publication Data
US 2014/0295506 A1    Oct. 2, 2014

(30) Foreign Application Priority Data

Nov. 11, 2011  (MY) .......................... PI 2011005479

(51) Int. Cl.
*C12P 13/00* (2006.01)
*C12P 13/02* (2006.01)

(52) U.S. Cl.
CPC *C12P 13/00* (2013.01); *C12P 13/02* (2013.01)

(58) Field of Classification Search
None
See application file for complete search history.

(56) References Cited

PUBLICATIONS

Mohamad et al. J. Oleo Science (2008) 57 (5) 263-267.*
Carpenter et al. (2010) Green Chemistry 2010, 12 2012-2018.*
Toliwal et al. Arch. Appl. Sci. Res. (2009) 1 (2) 344-355.*
Maznee et al. J. Oleo Sci. (2012) 61 (5) 297-302.*

* cited by examiner

*Primary Examiner* — Nashaat Nashed
(74) *Attorney, Agent, or Firm* — Rothwell, Figg, Ernst & Manbeck, P.C.

(57) ABSTRACT

A method to produce hydrazide from triacylglycerol, the method includes steps of mixing vegetable oil with an organic solvent in a reactor forming a mixture, adding hydrazinemonohydrate into the mixture, stirring the mixture, adding catalyst, stirring the mixture to form hydrazide and separating the hydrazide from the mixture.

9 Claims, 3 Drawing Sheets

METHOD TO PRODUCE HYDRAZIDE

CROSS REFERENCE TO RELATED APPLICATION(S)

This application is a 35 U.S.C. §371 National Phase Entry Application from 371of PCT/MY2012/00270, filed Nov. 7, 2012, designating the United States, and also claims the benefit of Malaysian Application No. PI 2011005479, filed Nov. 11 2011. The disclosures of both application are incorporated herein in their entirety by reference.

FIELD OF INVENTION

The present invention relates to a method to produce hydrazide.

BACKGROUND OF INVENTION

Hydrazide is an organic compound known to be industrially beneficial i.e. as bioactive synthesis intermediates in pharmaceutical manufacturing, surfactants or polymerisation agents in chemical applications.

Various methods have been developed to prepare hydrazide i.e. through chemical synthesis which requires multiple steps, high temperatures and pressure, produced by-products. One of the most widely used method for hydrazide preparation is treating esters with hydrazine monohydrate where the reaction involves unreactive esters that generally require refluxing in a basic condition for a few hours. However, this method is hazardous as it is an energy-intensive reaction and could evoke decomposition of the desired products.

Other past efforts to prepare such useful hydrazide, and substituted derivatives thereof were described in U.S. Pat. Nos. 4,310,696, 4,435,600 and 4,954,655. However, these methods are found to be costly, time consuming, and labour intensive.

In the recent years, enzymatic processes have become a preferred alternative to produce hydrazide. This is largely due to the advantages of enzymatic reactions which do not require high operating temperatures or high-pressured conditions and are less energy-intensive than chemical catalyst-dependant processes. The enzymes also possess high specificity and high selectivity toward substrates. This prevents production of undesired by-products during the reaction, thus, making enzymatic processes clean from undesired by-products, less hazardous and environment-friendly.

Accordingly, a need exists for a method to produce hydrazide using enzymatic route, providing solution to disadvantages as described in prior art.

SUMMARY OF INVENTION

Accordingly, the present invention relates to a method to produce hydrazide from triacylglycerol, the method includes steps of mixing vegetable oil with an organic solvent in a reactor forming a mixture, adding hydrazine monohydrate into the mixture, stirring the mixture at a temperature ranging from 30° C. to 50° C., for a period between 18 hours to 22 hours, adding catalyst Lipozyme® RMIM (an immobilized lipase from *Rhizomucor miehei*)of a loading from 3% to 7% into the mixture, stirring the mixture at a speed ranging from 350 rpm to 450 rpm to form hydrazide and separating the hydrazide from the mixture.

BRIEF DESCRIPTION OF DRAWINGS

The drawings constitute part of this specification and include an exemplary or preferred embodiment of the invention, which may be embodied in various forms. It should be understood, however, the disclosed preferred embodiments are merely exemplary of the invention. Therefore, the figures disclosed herein are not to be interpreted as limiting, but merely as the basis for the claim and for teaching one skilled in the art of the invention.

In the appended drawings.

DETAILED DESCRIPTION OF PREFERRED EMBODIMENTS

Figure 1:
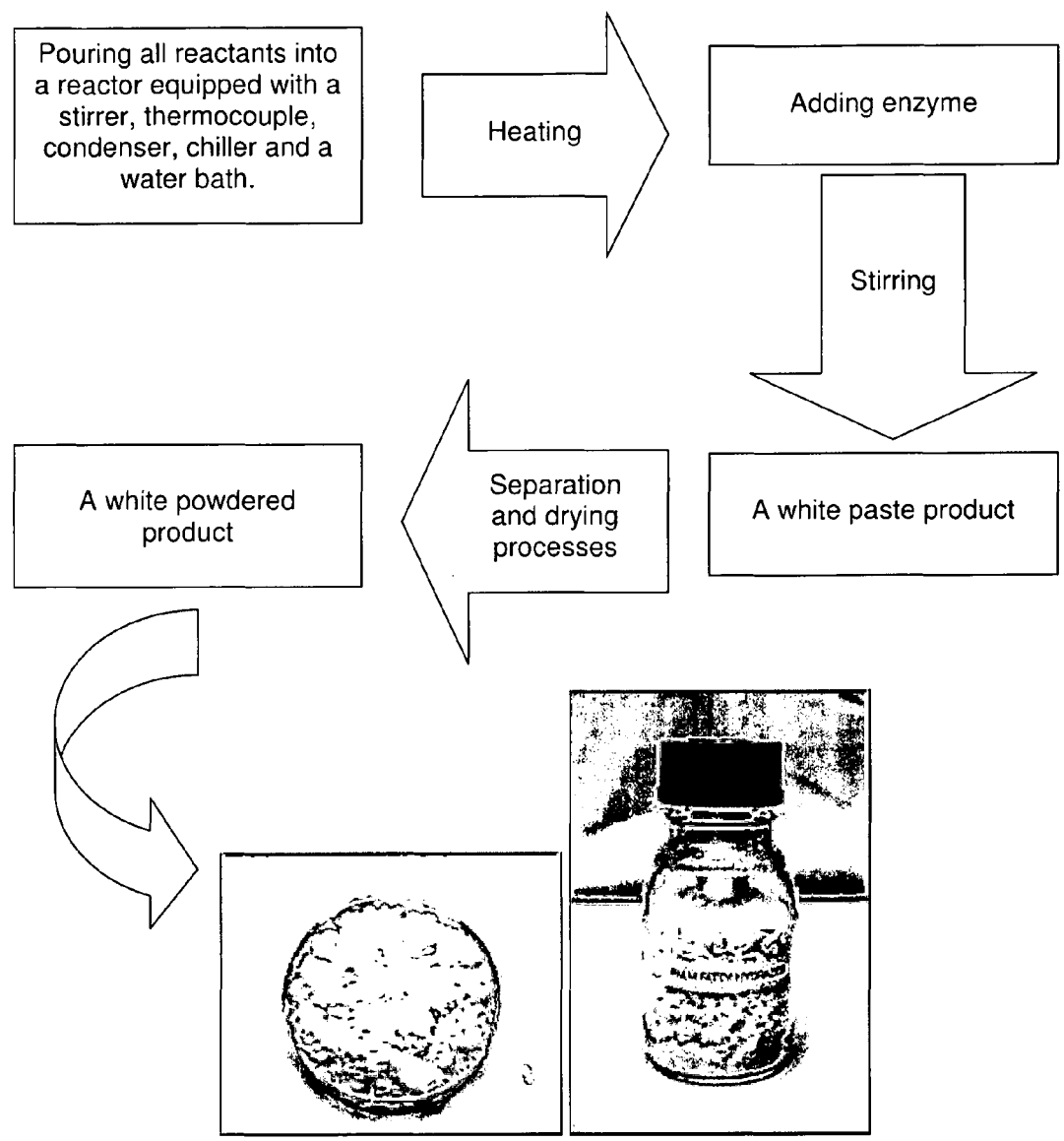
FIG. 1 illustrates a method to produce hydrazide through enzymatic route.
Figure 2:
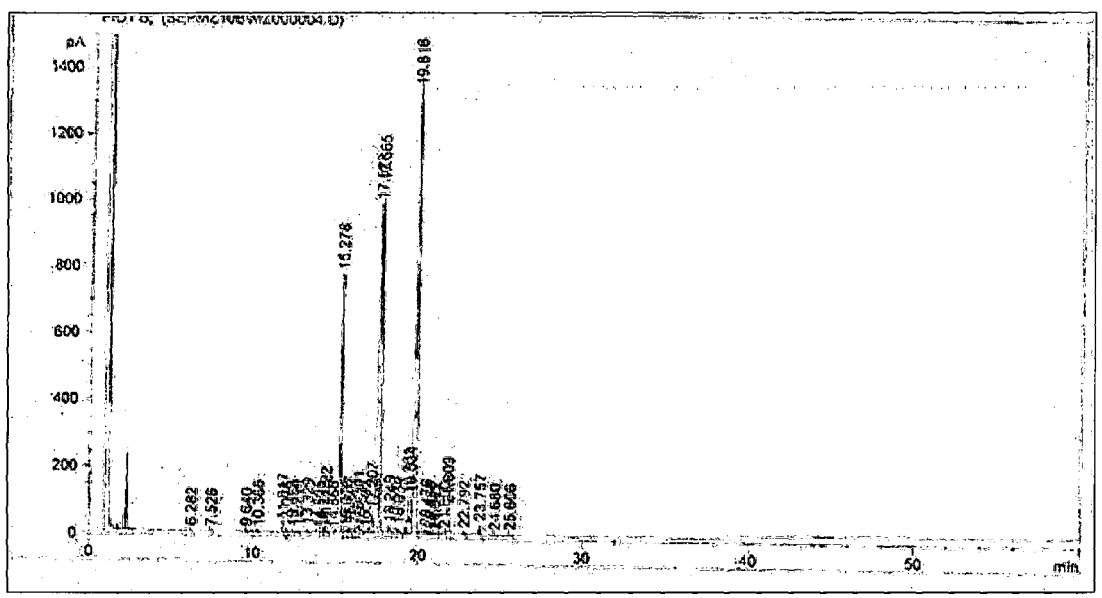
FIG. 2 illustrates a GC chromatogram of hydrazide produced from RBD palm oil.
Figure 3:
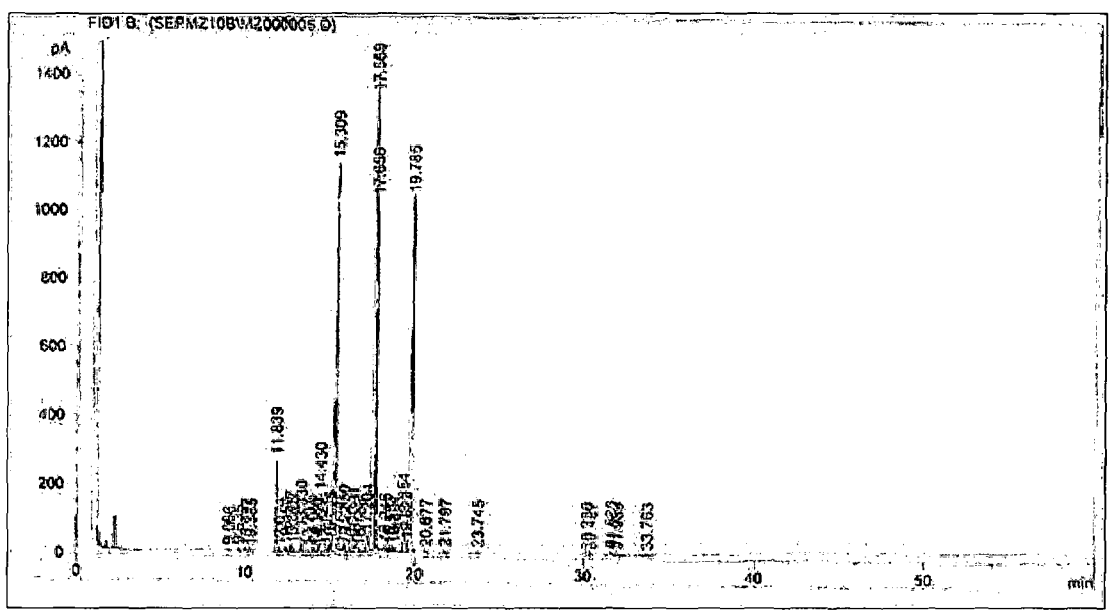
FIG. 3 illustrates a GC chromatogram of hydrazide produced from soy bean oil.

Detailed descriptions of preferred embodiments of the present invention are disclosed herein. It should be understood, however, that the embodiments are merely exemplary of the present invention, which may be embodied in various forms. Therefore, the details disclosed herein are not to be interpreted as limiting, but merely as the basis for the claim and for teaching one skilled in the art of the invention.

Particularly, the present invention relates to a method to produce hydrazide. More particularly, the present invention provides a method for the production of hydrazide directly from triacylglycerol by way of enzymatic route using Lipozyme RMIM lipase as a catalyst. The vegetable oils used in the process include but not limiting to palm oil, canola oil, sesame oil, olive oil, corn oil, soybean oil, sunflower oil and rapeseed oil.

Production of hydrazide direct from triacylglycerol using lipase, Lipozyme RMIM through one pot reaction, in solvent medium, particularly n-hexane at optimum reaction conditions i.e. mole ratio of oil to hydrazine monohydrate of 1 mmole of oil to 15 mmole of hydrazine hydrate, preferably, 1 mmole of oil to 11 mmole of hydrazine monohydrate, reaction temperature of 30 to 50° C., preferably at 40° C., reaction time of 18 to 22 hours, preferably at 20 hours, stirring speed of 350 to 450 rpm, preferably at 400 rpm and percentage of enzyme (Lipozyme RMIM) of 3 to 7%, preferable at 5% w/w were carried out in a reactor.

Typically, production of hydrazide direct from triacylglycerol through one pot method was carried out where hydrazine monohydrate is used at pH 12.

Ethanol is used in the separation process in order to separate hydrazide in n-hexane from Lipozyme RMIM at temperature ranging from 60 to 80° C. The separated hot hydrazide was left to cool for at least three hours at ambient temperature of 28° C. before continuing with filtration process. Unlike conventional methods, recrystallization of the hydrazide is not required in this present invention.

The following examples further illustrate but by no means limit the scope of present invention:

EXAMPLE 1

RBD Palm Olein 100 g of refined, bleached and deodorized palm olein was discharged into 2-L jacketed glass reactor (equipped with a circulating water bath to control temperature, a chiller and condenser to prevent solvent evaporation and a thermocouple to monitor temperature of the reaction) containing 400 mL of n-hexane. Accordingly, 122.5 g of hydrazine monohydrate at pH 12 was added into the reactor. The temperature of the mixture was set at 40° C. Once the temperature of the mixture reached the set temperature, the desired amount of enzyme (Lipozyme RMIM) was added into the reaction mixture. The stirring speed was set at 400 rpm and the reaction was run for 20 hours. After 20 hours of reaction, a white milky paste was discharged from the reactor. A 1-L beaker containing the discharged product was heated at 60 to 80° C. in the presence of ethanol to separate the product from the enzyme. A hot liquid mixture was left to cool for at least three hours at ambient temperature at 28° C. for crystallization process. Finally, a white paste product was formed. Before drying under vacuum, about 300 to 400 mL of ethanol was added into the white paste product to ease filtration process. After drying, a white-solid hydrazide is obtained. The conversion of fatty acid to fatty hydrazide is 99%.

EXAMPLE 2

Soya Bean Oil 100 g of soya bean oil was discharged into 2-L jacketed glass reactor (equipped with a circulating water bath to control temperature, a chiller and condenser to prevent solvent evaporation and a thermocouple to monitor temperature of the reaction) containing 400 mL of n-hexane. Accordingly, 112.3 g of hydrazine monohydrate was added into the reactor. The temperature of the mixture was set at 40° C. Once the temperature of the mixture reached the set temperature, the desired amount of enzyme (Lipozyme RMIM) was added into the reaction mixture. The stirring speed was set at 400 rpm and the reaction was run for 20 hours. After 20 hours of reaction, a white milky paste was discharged from the reactor. A 1-L beaker containing the discharged product was heated at 60 to 80° C. in the presence of ethanol to separate the product from the enzyme. A hot liquid mixture was left to cool for at least three hours at ambient temperature (28° C.) for crystallization process. Finally, a white paste product was formed. Before drying under vacuum, about 300 to 400 mL of ethanol was added into the white paste product to ease filtration process. After drying, a white-solid hydrazide is obtained. The conversion of fatty acid to fatty hydrazide is 97%.

EXAMPLE 3

Glyceryl Trioleate 100 g of glyceryl trioleate was discharged into 2-L jacketed glass reactor (equipped with a circulating water bath to control temperature, a chiller and condenser to prevent solvent evaporation and a thermocouple to monitor temperature of the reaction) containing 400 mL of n-hexane. Then, about 112.3 g of hydrazine monohydrate was added into the reactor. The temperature of the mixture was set at 40° C. Once the temperature of the mixture reached the set temperature, the desired amount of enzyme (Lipozyme RMIM) was added into the reaction mixture. The stirring speed was set at 400 rpm and the reaction was run for 20 hours. After 20 hours of reaction, a white milky paste was discharged from the reactor. A 1-L beaker containing the discharged product was heated at 60 to 80° C. in the presence of ethanol to separate the product from the enzyme. A hot liquid mixture was left to cool for at least three hours at ambient temperature (28° C.) for crystallization process. Finally, a white paste product was formed. Before drying under vacuum, about 300 to 400 mL of ethanol was added into the white paste product to ease filtration process. After drying, a white-solid hydrazide is obtained. The conversion of fatty acid to fatty hydrazide is 96%.

EXAMPLE 4

Glyceryl Tristearate 100 g of glyceryl tristearate was discharged into 2-L jacketed glass reactor (equipped with a circulating water bath to control temperature, a chiller and condenser to prevent solvent evaporation and a thermocouple to monitor temperature of the reaction) containing 400 mL of n-hexane. Accordingly, 112.3 g of hydrazine monohydrate was added into the reactor. The temperature of the mixture was set at 40° C. Once the temperature of the mixture reached the set temperature, the desired amount of enzyme (Lipozyme RMIM) was added into the reaction mixture. The stirring speed was set at 400 rpm and the reaction was run for 20 hours. After 20 hours of reaction, a white milky paste was discharged from the reactor. A 1-L beaker containing the discharged product was heated at 60 to 80° C. in the presence of ethanol to separate the product from the enzyme. A hot liquid mixture was left to cool for at least three hours at ambient temperature (28° C.) for crystallization process. Finally, a white paste product was formed. Before drying under vacuum, about 300 to 400 mL of ethanol was added into the white paste product to ease filtration process. After drying, a white-solid hydrazide is obtained. The conversion of fatty acid to fatty hydrazide is 79%.

EXAMPLE 5

Different pH

For the effect of pH on hydrazide production, the pH of hydrazine monohydrate was varied i.e. 6, 7, 8, 10 and 12 (original pH of hydrazine monohydrate). In order to get the desired pH of hydrazine monohydrate, HCl, 37% was added dropwise until the desired pH is achieved (monitored using pH paper), except for pH 12.

100 g of refined bleached and deodorized palm olein was discharged into 2-L jacketed glass reactor (equipped with a circulating water bath to control temperature, a chiller and condenser to prevent solvent evaporation and a thermocouple to monitor temperature of the reaction) containing 400 mL of n-hexane. Accordingly, 122.5 g of hydrazine monohydrate (of different pHs) was added into the reactor. The temperature of the mixture was set at 40° C. Once the temperature of the mixture reached the set temperature, the desired amount of enzyme (Lipozyme RMIM) was added into the reaction mixture. The stirring speed was set at 400 rpm and the reaction was conducted for 20 hours. After 20 hours of reaction, pinky orange of low viscosity pastes to a milky white non-flowable pastes (depending on the pHs of the hydrazine monohydrate used) were discharged from the reactor. A 1-L beaker containing the discharged product was heated at 60 to 80° C. in the presence of ethanol to separate the product from the enzyme. A hot liquid mixture was left to cool for at least three hours at ambient temperature (28° C.) for crystallization process. Finally, a pinky orange or white paste product (depending of the pHs of hydrazine monohydrate used) was formed. Before drying under vacuum, about 300 to 400 mL of ethanol was added into the pinky orange or white paste product to ease filtration process. After drying, a pinky orange or a white-solid hydrazide is obtained. The amounts of dried products obtained are varied depending on the pH of hydrazine monohydrate used as indicated in the table below:

TABLE 1

Amount of hydrazide obtained from different pHs of hydrazine monohydrate

| pH | Hydrazide | Appearance |
|---|---|---|
| pH 6 | No reaction has been observed | — |
| pH 7 | 58.65 g | Pinky orange powder |
| pH 8 | 89.03 g | Yellowish powder |
| pH 10 | 67.42 g | White powder |
| pH 12 | 62.21 g | White powder |

EXAMPLE 6

Different Percentage of Enzyme

Two sets of experiments were carried out for studying the effect of enzyme loading on the yield of hydrazide i.e. using 5% and 6% enzyme.

100 g of refined bleached and deodorized palm olein was discharged into 2-L jacketed glass reactor (equipped with a circulating water bath to control temperature, a chiller and condenser to prevent solvent evaporation and a thermocouple to monitor temperature of the reaction) containing 400 mL of n-hexane. Accordingly, 122.5 g of hydrazine monohydrate (of different pHs) was added into the reactor. The temperature of the mixture was set at 40° C. Once the temperature of the mixture reached the set temperature, the desired amount of enzyme (Lipozyme RMIM) i.e. 5 or 6% was added into the reaction mixture. The stirring speed was set at 400 rpm and the reaction was conducted for 20 hours. After 20 hours of reaction, pinky orange of low viscosity pastes to a milky white non-flowable pastes (depending on the pHs of the hydrazine monohydrate used) were discharged from the reactor. A 1-L beaker containing the discharged product was heated at 60 to 80° C. in the presence of ethanol to separate the product from the enzyme. A hot liquid mixture was left to cool for at least three hours at ambient temperature (28° C.) for crystallization process. Finally, a pinky orange or white paste product (depending of the pHs of hydrazine monohydrate used) was formed. Before drying under vacuum, about 300 to 400 mL of ethanol was added into the pinky orange or white paste product to ease filtration process. After drying, a pinky orange or a white-solid hydrazide is obtained. The amounts of dried products obtained are varied depending on the pHs of hydrazine monohydrate used as indicated in the table below:

TABLE 2

Amount of hydrazide obtained from two different percentages of enzymes

| Hydrazine | 5% enzyme | 6% enzyme |
|---|---|---|
| pH 7 | 58.65 g | 49.14 |
| pH 8 | 89.03 g | 69.67 g |
| pH 10 | 67.42 g | 65.88 g |
| pH 12 | 62.21 g | 61.53 g |

All the hydrazides obtained were characterized using FTIR as an identification tool where the formation of palm fatty hydrazides was confirmed by the presence of primary amine stretching in the region of 3316 and 3290 $cm^{-1}$ due to the asymmetrical and symmetrical N—H. The band at 3200 $cm^{-1}$ was due to the Fermi resonance band between the symmetric stretching modes of hydrogen-bonded $NH_2$ group. While, the stretching of amide carbonyl group and N—H bending of primary amine were observed at frequencies of 1628 $cm^{-1}$ and 1534 $cm^{-1}$, respectively. At different pHs, the intensities of the above-mentioned peaks are differed depending on the purity of the product obtained. Hydrazine monohydrate of pH 12 shows the best pH for synthesis of hydrazide followed by hydrazine monohydrate at pHs 10 and 8. This is because no further purification or recrystallization process is needed for the hydrazide obtained using hydrazine monohydrate of pH 12. The appearance of the product is white in colour, very fine and fluffy powder. The hydrazides obtained at other pHs required further purification especially hydrazides prepared at the pHs 7, 8 and 10.

While embodiments and examples of the present invention have been illustrated and described, it is not intended that these embodiments and examples illustrate and describe all possible forms of the present invention. Rather, words used in the specification are words of description rather than limitation and various changes may be made without departing from the scope of the invention.

The invention claimed is:

1. A method to produce hydrazide from triacylglycerol, comprising:
   i) mixing vegetable oil with an organic solvent in a reactor forming a mixture;
   ii) adding hydrazine monohydrate at pH 12 into the mixture;
   iii) stirring the mixture at a temperature ranging from 30° C. to 50° C., for a period between 18 hours to 22 hours;
   iv) adding from 3% to 7% w/w of an immobilized lipase from *Rhizomucor miehei* into the mixture;
   v) stirring the mixture at a speed ranging from 350 rpm to 450 rpm to form hydrazide; and
   vi) separating the hydrazide from the mixture.

2. The method of claim 1, wherein the vegetable oil comprises palm oil, canola oil, sesame oil, olive oil, corn oil, soybean oil, sunflower oil or rapeseed oil, or a mixture thereof.

3. The method of claim 1, wherein the organic solvent in step (i) comprises n-hexane.

4. The method of claim 1, wherein the mixture in step (i) is of a ratio ranging from 1 mmole of oil to 15 mmole of hydrazine monohydrate.

5. The method of claim 4, wherein the ratio is ranging from 1 mmole of oil to 11 mmole of hydrazine monohydrate.

6. The method of claim 1, wherein step (iii) is conducted at 40° C. for 20 hours.

7. The method of claim 1, wherein the catalyst loading in step (iv) is 5% w/w.

8. The method of claim 1, wherein step (v) is conducted at the speed of 400 rp.

9. The method of claim 1, wherein the method further comprises heating the hydrazide at 60 to 80° C in the presence of ethanol prior to step vi).

* * * * *